(12) United States Patent
Singh et al.

(10) Patent No.: US 8,637,283 B2
(45) Date of Patent: Jan. 28, 2014

(54) PRODUCTION OF HYDROCARBONS IN MICROORGANISMS

(75) Inventors: Abhay Kumar Singh, Chesterfield, MO (US); Ganesh M. Kishore, Saint Louis, MO (US)

(73) Assignee: Mogene LC, St. Louis, MO (US)

( * ) Notice: Subject to any disclaimer, the term of this patent is extended or adjusted under 35 U.S.C. 154(b) by 255 days.

(21) Appl. No.: 13/005,691

(22) Filed: Jan. 13, 2011

(65) Prior Publication Data

US 2011/0177575 A1 Jul. 21, 2011

Related U.S. Application Data

(60) Provisional application No. 61/295,502, filed on Jan. 15, 2010.

(51) Int. Cl.

| *C12P 5/00* | (2006.01) |
| *C12Q 1/68* | (2006.01) |
| *C12N 9/02* | (2006.01) |
| *C12N 9/00* | (2006.01) |
| *C12N 1/20* | (2006.01) |
| *C12N 15/00* | (2006.01) |
| *C07H 21/04* | (2006.01) |

(52) U.S. Cl.
USPC ............ 435/166; 435/6.1; 435/189; 435/183; 435/252.3; 435/320.1; 435/252.34; 435/440; 536/23.2

(58) Field of Classification Search
None
See application file for complete search history.

(56) References Cited

U.S. PATENT DOCUMENTS

| 6,511,939 | B1 | 1/2003 | Burns et al. |
| 7,579,164 | B2 | 8/2009 | Bender et al. |
| 2007/0264691 | A1 | 11/2007 | Penaloza-Vazquez et al. |

FOREIGN PATENT DOCUMENTS

| WO | WO 2007/127835 | 11/2007 |
| WO | WO 2010/001078 | 1/2010 |

OTHER PUBLICATIONS

Piotrowski et al. Primary or secondary? Versatile nitrilases in plant metabolism. Phytochemistry. Nov. 2008;69(15):2655-67.*
Q6L6S0—UniProt Database. 2004.*
Stewart et al Biotechnology and Genetic Engineering Reviews, 14:67-143, 1997.*
GenBank accession No. AA058146 (gi: 28855085) dated Mar. 28, 2011, 2 pages.
GenBank accession No. AA058147 (gi: 28855086) dated Mar. 28, 2011, 2 pages.
GenBank accession No. AAC46032 (gi: 2673890) dated Dec. 11, 1997, 1 page.
GenBank accession No. AE016853 (gi: 28856110) dated Mar. 28, 2011, 1 page.
GenBank accession No. AY391839 (gi: 37575137) dated Dec. 17, 2003, 3 pages.
GenBank accession No. NP_794451 (gi: 28871832) dated Feb. 4, 2011, 2 pages.
GenBank accession No. NP_794452 (gi: 28871833) dated Feb. 4, 2011, 2 pages.
GenBank accession No. NP_794453 (gi: 28871834) dated Feb. 4, 2011, 2 pages.
GenBank accession No. NP_794454 (gi: 28871835) dated Feb. 4, 2011, 2 pages.
GenBank accession No. NP_794455 (gi: 28871836) dated Feb. 4, 2011, 1 page.
GenBank accession No. NP_794456 (gi: 28871837) dated Feb. 4, 2011, 2 pages.
GenBank accession No. U14657 (gi: 2673889) dated Dec. 11, 1997, 4 pages.
GenBank accession No. YP_003450258 (gi: 288959918) dated Feb. 17, 2010, 1 page.
GenBank accession No. YP_003450259 (gi: 288959919) dated Feb. 17, 2010, 1 page.
GenBank accession No. ZP_04586947 (gi: 237798486) dated Apr. 29, 2011 1 page.
GenBank accession No. ZP_04586949 (gi: 237798488) dated Dec. 10, 2010, 1 page.
GenBank accession No. ZP_04586951 (gi: 237798490) dated Apr. 29, 2011 1 page.
GenBank accession No. ZP_04586952 (gi: 237798491) dated Apr. 29, 2011 1 page.
GenBank accession No. ZP_06460769 (gi: 289627815) dated Dec. 10, 2010, 1 page.
GenBank accession No. ZP_06460770 (gi: 289627816) dated Dec. 10, 2010, 1 page.
GenBank accession No. ZP_06460771 (gi: 289627817) dated Dec. 10, 2010, 1 page.
GenBank accession No. ZP_06460773 (gi: 289627819) dated Dec. 10, 2010, 1 page.
GenBank accession No. ZP_06460774 (gi: 289627820) dated Dec. 10, 2010, 1 page.
GenBank accession No. ZP_06482565 (gi: 289651222) dated Dec. 10, 2010, 1 page.
GenBank accession No. ZP_06482566 (gi: 289651223) dated Dec. 10, 2010, 1 page.
GenBank accession No. ZP_06482567 (gi: 289651224) dated Dec. 10, 2010, 1 page.
GenBank accession No. ZP_06482572 (gi: 289651229) dated Dec. 10, 2010, 1 page.
GenBank accession No. ZP_07234587 (gi: 301386169) dated Dec. 10, 2010, 1 page.
GenBank accession No. ZP_07234588 (gi: 301386170) dated Dec. 10, 2010, 1 page.
GenBank accession No. ZP_07234760 (gi: 301386342) dated Dec. 10, 2010, 1 page.
GenBank accession No. ZP_07235048 (gi: 301386630) dated Dec. 10, 2010, 1 page.
GenBank accession No. ZP_07252112 (gi: 302060571) dated Dec. 10, 2010, 1 page.
GenBank accession No. ZP_07252113 (gi: 302060572) dated Dec. 10, 2010, 1 page.

(Continued)

*Primary Examiner* — Yong Pak
(74) *Attorney, Agent, or Firm* — Fish & Richardson P.C.

(57) ABSTRACT

A recombinant microorganism employing a bacterial pathway to produce a cyclic amino acid (e.g., coronamic acid or norcoronamic acid) and a plant enzyme (ACC oxidase) to oxidize the amino acid and produce an alkene (e.g., 1-butene or propene) is provided herein. Expression of these two biosynthetic modules in various microbial chassis will facilitate alkene production from diverse energy and carbon sources, including sugars, glycerol, $CO_2$, $CH_4$, $H_2$, and sunlight.

14 Claims, 4 Drawing Sheets

(56) References Cited

OTHER PUBLICATIONS

GenBank accession No. ZP_07252114 (gi: 302060573) dated Dec. 10, 2010, 1 page.

Alfano et al., "The Pseudomonas syringae Hrp pathogenicity island has a tripartite mosaic structure composed of a cluster of type III secretion genes bounded by exchangeable effector and conserved effector loci that contribute to parasitic fitness and pathogenicity in plants," *Proc Natl Acad Sci USA*, 2000, 97:4856-4861.

Ali & Murrell, "Development and validation of promoter-probe vectors for the study of methane monooxygenase gene expression in *Methylococcus capsulatus* Bath," *Microbiology*, 2009, 155:761-771.

Atsumi et al., "Directed evolution of *Methanococcus jannaschii* citramalate synthase for biosynthesis of 1-propanol and 1-butanol by *Escherichia coli*". *Appl. Environ Microbiol.*, 2008, 74:7802-7808.

Atsumi et al., "Direct photosynthetic recycling of carbon dioxide to isobutyraldehyde," *Nat. Biotech.*, 2009, 27: 1177-1178.

Bateman et al., "Pfam 3.1: 1313 multiple alignments and profile HMMs match the majority of proteins," *Nucl. Acids Res.*, 1999, 27:260-262.

Bender et al., "*Pseudomonas syringae* phytotoxins: mode of action, regulation and biosynthesis by peptide and polyketide synthetases," *Microbiol Mol Biol Rev.*, 1999, 63:266-292.

Bender et al., "Characterization of the genes controlling biosynthesis of the polyketide phytotoxin coronatine including conjugation between coronafacic and coronamic acid," *Gene*, 1993, 133:31-38.

Bertani et al., "Controlled specific expression and purification of 6 × His-tagged proteins in *Pseudomonas*," *FEMS Microbiol Lett.*, 1999, 179:101-106.

Blume and Grierson, "Expression of ACC oxidase promoter ± GUS fusions in tomato and *Nicotiana plumbaginifolia* regulated by developmental and environmental stimuli," *Plant J.*, 1997, 12:731-746.

Brooks et al., "Identification and characterization of a well-defined series of coronatine biosynthetic mutants of *Pseudomonas syringae* pv. *tomato* DC3000," *Mol. Plant Microbe Inter.*, 2004, 17: 162-174.

Buell et al., "The complete genome sequence of the *Arabidopsis* and tomato pathogen *Pseudomonas syringae* pv. *tomato* DC3000," *Proc. Natl. Acad. Sci. USA*, 2003, 100:10181-10186.

Couch et al., "Characterization of CmaA, an Adenylation-Thiolation Didomain Enzyme Involved in the Biosynthesis of Coronatine," *J. Bacteriol.*, 2004, 186:35-42.

Cuppels, "Generation and Characterization of Tn5 Insertion Mutations in *Pseudomonas syringae* pv. *tomato*," *Appl. Environ. Microbiol.*, 1986, 52:323-327.

Elišáková et al., "Feedback-resistant acetohydroxy acid synthase increases valine production in *Corynebacterium glutamicum*," *Applied and Environ, Microbiol.*, 2005, 71:207-213.

Gross and Loper, "Genomics of secondary metabolite production by *Pseudomonas* spp," *Nat. Prod. Rep.*, 2009, 26:1408-1446.

Hamilton et al., "Identification of a tomato gene for the ethylene-forming enzyme by expression in yeast," *PNAS*, Aug. 15, 1991, 88(16):7434-7437.

Hashiguchi et al., "Construction of an L-isoleucine overproducing strain of *Escherichia coli* K-12," *Biosci Biotechnol Biochem.*, 1999, 63:672-679.

Kovach et al. "Four new derivatives of the broad-host-range cloning vector pBBR1MCS, carrying different antibiotic-resistance cassettes," *Gene*, 1995, 166:175-176.

Lu et al., "Construction of pMEKm12, an expression vector for protein production in *Pseudomonas syringae*," *FEMS Microbiol Lett.*, 2002, 210:115-121.

Mamer, "Initial catabolic steps of isoleucine, the R-pathway and the origin of alloisoleucine," *Chromatography*, 2001, 758:49-55.

Mellgren et al., "Mqo, a tricarboxylic acid cycle enzyme, is required for virulence of *Pseudomonas syringae* pv. *tomato* strain DC3000 on *Arabidopsis thaliana*," *J Bacteriol.*, 2009, 191:3132-3141.

Murrel and Dalton, "Nitrogen Fixation in Obligate Methanotrophs," *J Gen Microbiol.*, 1983, 129:3481-3486.

Ng et al., "*phrA*, the major photoreactivating factor in the cyanobacterium *Synechocystis* sp. strain PCC 6803 codes for a cyclobutane-pyrimidine-dimer-specific DNA photolyase," *Arch Microbiol.*, 2000, 173:412-417.

Palmer et al., "Effects of Environmental and Nutritional Factors on Production of the Polyketide Phytotoxin Coronatine by *Pseudomonas syringae* pv. Glycinea," *Appl. Environ Microbiol.*, 1993, 59:1619-1626.

Park et al., "Metabolic engineering of *Escherichia coli* for the production of L-valine based on transcriptome analysis and in silico gene knockout simulation," *Proc. Natl. Acad. Sci.*, 2007, 104: 7797-7802.

Parry et al., "Biosynthesis of coronatine: investigations of the biosynthesis of coronamic acid," *J. Am. Chem. Soc.*, 1991, 113 (5), pp. 1849-1850.

Patel et al., "Investigations of coronatine biosynthesis. Overexpression and assay of CmaT, a thioesterase involved in coronamic acid biosynthesis," *Tetrahedron*, 1998, 54:15927-15936.

Penaloza-Vazquez et al., "Regulatory interactions between the Hrp type III protein secretion system and coronatine biosynthesis in *Pseudomonas syringae* pv. tomato DC3000," *Microbiology*, 2000, 146:2447-2456.

Rangaswamy et al., "Biosynthesis of the *Pseudomonas* polyketide coronafacic acid requires monofunctional and multifunctional polyketide synthase proteins," *Proc Natl Acad Sci USA*, 1998, 95:15469-15474.

Rey et al., "Regulation of uptake hydrogenase and effects of hydrogen utilization on gene expression in *Rhodopseudomonas palustris*," *J. Bacteriol.*, 2006, 188(17):6143-6152.

Sonnhammer et al., "Pfam: multiple sequence alignments and HMM-profiles of protein domains," *Nucl. Acids Res.*, 1998, 26:320-322.

Sonnhammer et al., "Pfam: A comprehensive database of protein domain families based on seed alignments," *Proteins*, 1997, 28:405-420.

Stolyar et al., "Role of multiple gene copies in particulate methane monooxygenase activity in the methane-oxidizing bacterium *Methylococcus capsulatus* Bath," *Microbiology*, 1999, 145:1235-1244.

Ullrich and Bender, "The biosynthetic gene cluster for coronamic acid, an ethylcyclopropyl amino acid, contains genes homologous to amino acid-activating enzymes and thioesterases," *J. Bacteriol.*, 1994, 176:7574-7586.

Ullrich et al., "Cloning and expression of genes required for coronamic acid (2-ethyl-1-aminocyclopropane 1-carboxylic acid), an intermediate in the biosynthesis of the phytotox coronatine," *Applied and Environmental Microbiology*, Aug. 1994, 60(8):2890-2897.

Vaillancourt et al., "Cryptic chlorination by a non-haem iron enzyme during cyclopropyl amino acid biosynthesis," *Nature*, 2005, 436:1191-1194.

Wilson et al., "Apple ripening-related cDNA clone pAP4 confers ethylene-forming ability in transformed *Saccharomyces cerevisiae*," *Plant Physiology*, 1993, 102(3):783-788.

Whittenbury and Dalton, "The methylotrophic bacteria," *The Prokaryotes*, 1981, pp. 894-902.

Zhang et al., "Expression, purification and characterization of 1-aminocyclopropane-1-carboxylate oxidase from tomato in *Escherichia coli*" *Biochem J.*, Apr. 1995, 307(Pt 1):77-85.

Authorized Officer Mart Van De Kamp, International Search Report, PCT/US2011/021120, mailed Apr. 26, 2011, 6 pages.

Hoffman et al; Stereospecific Conversion of 1-Aminocyclopropanecarboxylic Acid to Ethylene by Plant Tissues; Plant Physiol; 1982; pp. 70:195-199.

Schafer et al; Small mobilizable multi-purpose cloning vectors derived from the *Escherichia coli* plasmid pK18 and pK19: selection of defined deletions in the chromosome of *Corynebacterium glutamicum*; Gene; 1994; pp. 145:69-73.

Tsuchida et al; Improvement of an 1-Leucine-Producing Mutant of *Brevibacterium lactofermentum* 2256 by Genetically Desensitizing It to a-Acetohydroxy Acid Synthetase; Appl Environ Microbiol.; 1986; pp. 51:1024-127.

* cited by examiner

```
ACCO        CATATGGAGAACTTCCCAATTATTAACTTGGAAAAGCTCAATGGAGATGAGAGAGCCAAC
ACCO_opt    CATATGGAGAACTTCCCGATCATCAATCTGGAGAAACTGAACGGCGACGAACGCGCGAAC
            *****************.**.**.**....****.**.**.**.**..**..*.**.***

ACCO        ACCATGGAAATGATCAAAGATGCTTGTCAGAATTGGGGCTTCTTTGAGTTGGTGAACCAT
ACCO_opt    ACCATGGAAATGATTAAGGATGCATGCCAGAATTGGGGTTTCTTCGAACTGGTCAATCAT
            **************.**.*****.**.**********.*****.**..****.**.***

ACCO        GGAATTCCACATGAAGTAATGGACACAGTAGAGAAAATGACAAAGGGACATTACAAGAAG
ACCO_opt    GGTATCCCGCACGAGGTGATGGATACGGTTGAGAAGATGACCAAGGGCCACTACAAAAAG
            **:**.**.**.**.**.*****.**.**.*****.*****.*****.**.*****.***

ACCO        TGCATGGAACAGAGGTTTAAGGAACTAGTGGCAAGTAAGGGACTTGAGGCTGTTCAAGCT
ACCO_opt    TGTATGGAACAGCGCTTTAAAGAGCTGGTGGCGAGCAAAGGTCTGGAAGCGGTCCAAGCT
            **.*********.*.*****.**.**.*****.**.**.**.**.**.**.**.******

ACCO        GAGGTTACTGATTTAGATTGGGAAAGCACTTTCTTCTTGCGCCATCTTCCTACTTCTAAT
ACCO_opt    GAAGTGACGGATTTGGACTGGGAGTCCACCTTCTTTCTGCGTCATTTGCCGACCAGCAAC
            **.**.**.**.*****.**.*****..:..***.*****.****.***.*.**.**.:.**

ACCO        ATCTCTCAAGTACCCGATCTTGACGAAGAATACAGAGAGGTGATGAGAGATTTTGCTAAA
ACCO_opt    ATTAGCCAAGTTCCGGATCTGGATGAAGAATACCGTGAGGTCATGCGTGACTTTGCGAAG
            **.:..*****:**.*****.**.*********.*:*****.***.*:**.*****.**.

ACCO        AGATTGGAGAAATTGGCTGAGGAGTTACTTGACTTACTCTGTGAAAATCTTGGACTTGAA
ACCO_opt    CGTCTGGAGAAGTTGGCAGAAGAGCTGCTGGATCTGCTGTGCGAGAACCTGGGCTTGGAG
            .*:.*******.*****.**:***.*.**.**.*.**.**.**.**.**.**.*.**.

ACCO        AAAGGTTACTTGAAAAATGCCTTTTATGGATCAAAAGGTCCCAACTTTGGTACTAAAGTT
ACCO_opt    AAGGGTTATCTGAAGAACGCCTTCTATGGCAGCAAGGGTCCGAATTTCGGTACGAAGGTG
            **.*****.****.**.*****.*****..:..**.*****.**.**.*****.**.**

ACCO        AGCAACTATCCACCATGTCCTAAGCCCGATTTGATCAAGGGACTCCGCGCTCATACAGAC
ACCO_opt    TCTAACTATCCGCCGTGTCCTAAACCGGACCTGATTAAGGGTTTGCGTGCACACACCGAT
            :.********.**.********.**.**..****.*****.:.*.**:**.**.**.**

ACCO        GCAGGAGGCATCATACTTCTGTTCCAAGATGACAAAGTGAGTGGCCTTCAACTCCTCAAA
ACCO_opt    GCAGGCGGTATCATCCTGCTGTTCCAGGACGACAAAGTTAGCGGTCTGCAACTGCTGAAA
            *****.**.*****.**.**.********.**.********.**.**.*****.**.***

ACCO        GACGAGCAATGGATCGATGTTCCTCCCATGCGCCACTCTATTGTGGTTAACCTTGGTGAC
ACCO_opt    GATGAACAGTGGATCGACGTCCCGCCGATGCGCCATTCGATTGTGGTGAATCTGGGCGAC
            **.**.**.*********.**.**.**.********.**.*******.**.**.**.***

ACCO        CAACTTGAGGTGATCACTAACGGGAAGTACAAGAGTGTGCTGCACAGAGTAATTGCACAA
ACCO_opt    CAGTTAGAAGTCATTACCAATGGCAAATACAAGAGCGTGCTGCACCGTGTTATTGCGCAG
            **..*:**.**.**.**.**.**.**.********.********.*:*:**.*****.**.

ACCO        ACAGACGGGACACGAATGTCATTAGCCTCATTTTACAATCCAGGAAGTGATGCAGTAATA
ACCO_opt    ACCGACGGTACGCGCATGAGCCTGGCTAGCTTTTACAATCCGGGTAGCGACGCCGTTATC
            **.*****.**.**.***:..*.**.:..*********.**:**.**.**.**.**:*

ACCO        TATCCAGCAAAAACTTTGGTTGAAAAGAGGCAGAGGAAAGTACACAAGTGTATCCAAAG
ACCO_opt    TATCCGGCGAAAACCCTGGTCGAGAAAAAGCAGAGGAGAGCACTCAAGTTTACCCGAAA
            *****.**.*****..****.**.**.**.*********:**.*****.**.**.**.

ACCO        TTTGTGTTTGATGATTACATGAAGTTATATGCTGGACTCAAGTTTCAAGCCAAAGAGCCA
```

FIGURE 2-1

```
ACCO_opt    TTTGTTTTTGATGATTACATGAAACTGTACGCAGGTCTGAAGTTCCAGGCGAAGGAACCA
            *****.*****************. *.** **:**:** ***** **.** **.**.***

ACCO        AGATTTGAAGCAATGAAGGCAATGGAAAGTGATCCAATTGCAAGTGCTTAGGTACC
ACCO_opt    CGTTTTGAGGCTATGAAGGCTATGGAGAGCGATCCGATTGCCTCCGCGTAGGTACC
            .*:*****.**:********:*****.** *****.*****.:  ** ********
```

FIGURE 2-2

PRODUCTION OF HYDROCARBONS IN MICROORGANISMS

RELATED APPLICATIONS

This application claims the benefit of U.S. Provisional Application No. 61/295,502, filed Jan. 15, 2010, which is incorporated herein by reference in its entirety.

TECHNICAL FIELD

This disclosure relates to the production of hydrocarbons using recombinant microorganisms. In particular, this disclosure relates to the production of alkenes such as 1-butene and/or propene by recombinant microorganisms.

BACKGROUND

Petroleum is facing declining global reserves and contributes to more than 30% of greenhouse gas emissions driving global warming. Global consumption of petroleum in the form of transportation fuel reaches 800 billion barrels annually. Diesel and jet fuels account for greater than 50% of global transportation fuels.

Due to increasing petroleum costs and reliance on petrochemical feedstocks, the chemicals industry is also looking for ways to improve margin and price stability, while reducing its environmental footprint. One way to accomplish these goals is through the development of greener products that are more energy, water, and $CO_2$ efficient than current products. Fuels produced from biological sources represent one such process.

Overall reserves of fossil fuels are dwindling and extraction of fossil fuels from known reserves is becoming increasingly more costly and complex. Biologically-produced hydrocarbons have the potential to replace society's dependence on such fossil fuels. Hydrocarbons have high energy density, are compatible with existing infrastructure including transport and storage facilities, and constitute a source of both energy and materials like plastics and specialty chemicals.

SUMMARY

Provided herein is a recombinant microorganism, comprising one or more coronamic acid biosynthesis genes whose expression results in production of coronamic and norcoronamic acids; and a gene encoding an ACC oxidase (EC 1.14.17.4), wherein at least one of said genes is a recombinant gene. The one or more coronamic acid biosynthesis genes can be an L-isoleucine or L-valine isomerase and a coronamic acid synthase.

The recombinant microorganism can include additional genes. For example, the recombinant microorganism can further comprise a gene encoding a β-cyanoalanine synthase (EC 4.4.1.9) and a gene encoding a nitrilase (EC 3.5.5.1) While in other embodiments, the recombinant microorganism can further comprise one or more of the following: a gene encoding an alanine dehydrogenase (EC 1.4.1.1), a gene encoding a glutamate dehydrogenase (EC 1.4.1.2), a gene encoding a serine O-acetyl transferase (EC 2.3.1.30), a gene encoding a threonine dehydratase (EC4.3.1.19), a gene encoding a homoserine dehydratase (EC 4.4.1.1), a gene encoding a citramalate synthase (EC 4.1.3.22). In some embodiments, a recombinant microorganism can further comprise genes encoding GDP mannose synthase (mannose-1-phosphate guanylyltransferase; EC 2.7.7.22), GDP D-mannose epimerase (EC 5.1.3.18), GDP L-galactose pyrophosphorylase (EC 2.7.7.69), L-galactose dehydrogenase (EC 1.1.1.122) and L-galactonolactone dehydrogenase (EC 1.3.2.3).

A number of prokaryotes and eukaryotes are suitable for use in constructing the recombinant microorganisms described herein, e.g., Gram-negative bacteria, Gram-positive bacteria, yeast, fungi, and photosynthetic organisms. For example, the microorganism can be an *Escherichia coli, Saccharomyces cerevisiae, Synechocystis* 6803, *Synechococcus* 7002, *Methylomonas methanica, Methylococcus capsulatus,* or *Rhodopseudomonas palustris*.

The microorganism can also be of the genus *Pseudomonas*. In some embodiments, such a microorganism further comprises a gene that inhibits production of coronafacic acid, or comprising a null mutation in a coronafacic acid biosynthetic pathway gene.

Further provided herein is a method of producing 1-butene, comprising the steps of: a) growing a recombinant microorganism as described herein in a culture medium, under conditions in which the coronamic acid biosynthesis genes and the ACC oxidase gene are expressed; and b) recovering the 1-butene produced by said microorganism. Butene can be recovered by known methods, for example, 1-butene can be recovered as a volatile product from the gaseous components in the fermentor. In some embodiments, the microorganism is of the genus *Pseudomonas* and the culture medium comprises an inhibitor of coronafacic acid biosynthesis.

Also provided is a method of producing propene, the method comprising the steps of: a) growing a recombinant microorganism as described herein, wherein the microorganism further comprises a gene encoding a feedback resistant acetohydroxyacid synthase (EC 2.2.1.6), in a culture medium, under conditions in which the coronamic acid biosynthesis genes, the ACC oxidase gene and the feedback resistant acetohydroxyacid synthase gene are expressed; and b) recovering the propene produced by the microorganism. Propene can be recovered by known methods, for example, propene can be recovered as a volatile product from the gaseous components in the fermentor. In some embodiments, the microorganism is of the genus *Pseudomonas* and the culture medium comprises an inhibitor of coronafacic acid biosynthesis or is a mutant Pseudomonad that preferentially accumulates coronamic acid without further transformation.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is an alignment of the full-length nucleotide sequences of a codon-optimized ACC oxidase (ACCO_opt) with the native tomato ACC oxidase (ACCO).

Like reference symbols in the various drawings indicate like elements.

DETAILED DESCRIPTION

Figure 1:
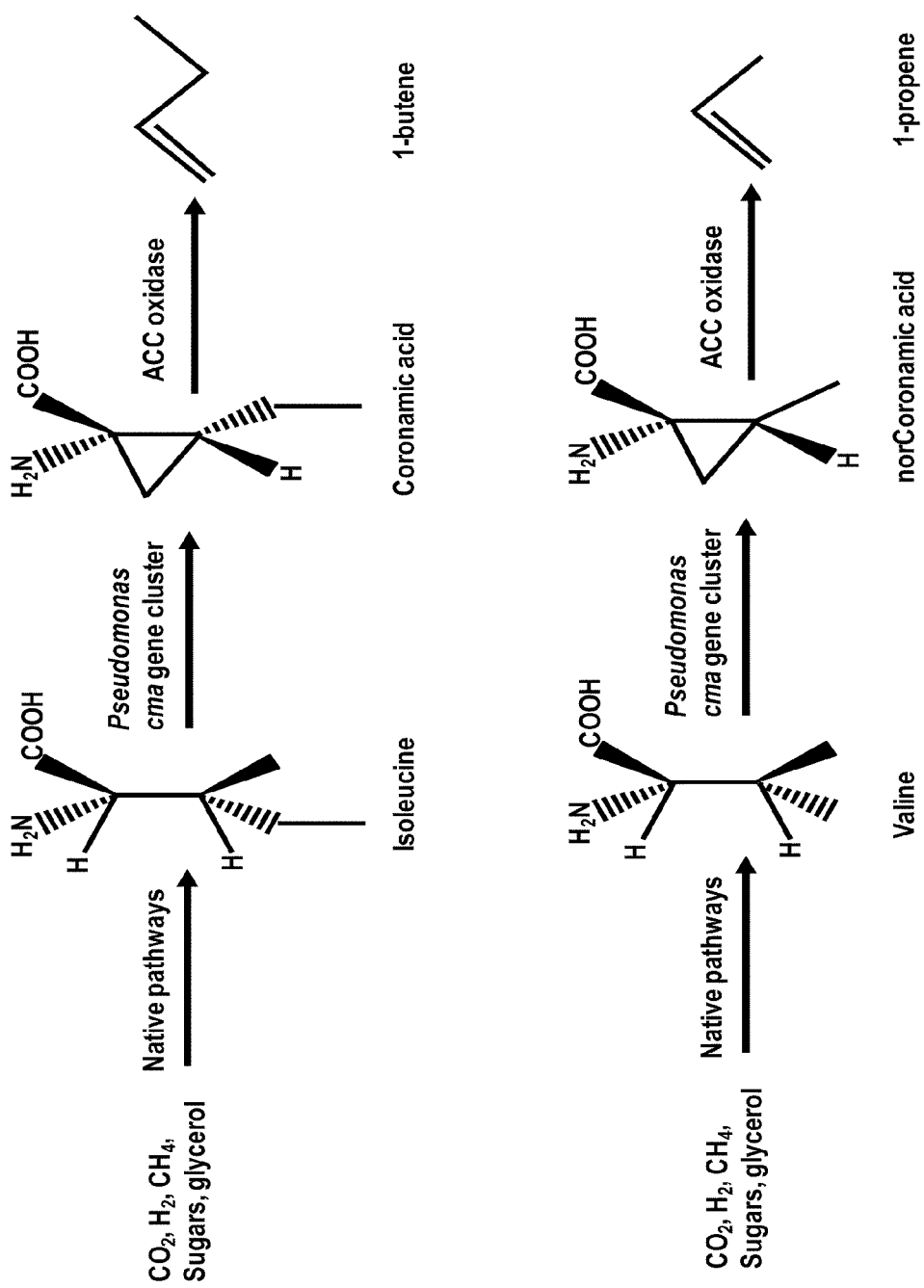
FIG. 1 is a scheme illustrating production of butene and propene in a recombinant microorganism using various feedstocks. Numbers indicate individual carbon atoms.

This document is based on the discovery that recombinant microorganisms expressing polypeptides involved in the biosynthesis of coronamic and norcoronamic acids, and expressing a 1-aminocyclopropane-1-carboxylate oxidase (ACC oxidase) can produce alkenes such as 1-butene or propene. Expression of these two biosynthetic modules in various microbial chassis allows alkenes to be produced from energy and carbon sources such as sugars, glycerol, $CO_2$, $CH_4$, $H_2$, and sunlight, rather than fossil fuels. See FIG. 1. At least one of the genes encoding these biosynthetic modules is a recombinant gene, the particular recombinant gene depending on the species or strain selected for use. Additional biosynthetic modules can be included in order to increase alkene yield, improve efficiency with which energy and carbon sources are converted to alkenes, and/or to facilitate larger scale alkene production by the microorganism during culture. Such additional biosynthetic modules include a gene encoding a β-cyanoalanine synthase and a gene encoding a nitrilase, these genes may be endogenous genes or recombinant genes.

As used herein, the term recombinant microorganism refers to a microorganism, the genome of which has been augmented by at least one incorporated DNA sequence. Such DNA sequences include but are not limited to genes that are not naturally present, DNA sequences that are not normally transcribed into RNA or translated into a protein ("expressed"), and other genes or DNA sequences which one desires to introduce into the non-recombinant microorganism. It will be appreciated that typically the genome of a recombinant microorganism described herein is augmented through the stable introduction of one or more recombinant genes that are not originally resident in the microorganism that is the recipient of the DNA. However, it is within the scope of the invention to isolate a DNA segment from a given microorganism, and to subsequently introduce one or more additional copies of that DNA back into the same microorganism, e.g., to enhance production of the product of a gene or alter the expression pattern of a gene. In some instances, the introduced DNA will modify or even replace an endogenous gene or DNA sequence by, e.g., homologous recombination or site-directed mutagenesis.

The term "recombinant gene" refers to a gene or DNA sequence that is introduced into a recipient microorganism, regardless of whether the same or a similar gene may already be present in such a microorganism. "Introduced," or "augmented" in this context, is known in the art to mean introduced or augmented by the hand of man. Thus, a recombinant gene may be a DNA sequence from another species, or may be a DNA sequence that originated from or is present in the same species, but has been incorporated into a microorganism by genetic engineering methods to form a recombinant microorganism. It will be appreciated that a recombinant gene that is introduced into a microorganism can be identical to a DNA sequence that is normally present in the microorganism being transformed, and is introduced to provide one or more additional copies of the DNA to thereby permit overexpression or modified expression of the gene product of that DNA.

Coronamic Acid Biosynthesis Polypeptides

Coronamic acid (1-amino-2-ethylcyclopropyl-1-carboxylic acid; CMA) is a cyclopropyl amino acid produced by certain phytopathogenic *Pseudomonas* species. Coronamic acid is a moiety found in the phytotoxin, coronatine. The bacterial pathway used to produce coronamic acid involves isomerization of L-isoleucine to L-allo-isoleucine, which is then oxidatively cyclized to form coronamic acid. A related compound, norcoronamic acid ((1S,2S)-2-methyl-1-aminocyclopropane-1-carboxylic acid; nCMA) is produced by cyclization of L-valine.

Conversion of allo-isoleucine to coronamic acid in *Pseudomonas* involves a cluster of genes, known as the cma cluster. See, e.g., US 2007/0264691; Gross, H. and Loper, J. E. (2009) Nat. Prod. Rep. 26: 1408-1446; Buell et al. Proc. Natl. Acad. Sci. USA 100:10181-10186 (2003); and Ullrich, M. and Bender, C. L. (1994) *J. Bacteriol* 176: 7574-7586). For example, a 7-10 kb region of a 90-kb plasmid designated p4180A in *P. syringae* pv. *glycinea* PG4180 contains co-transcribed genes sufficient to convert allo-isoleucine to coronamic acid. As another example, a cluster of chromosomally encoded genes from *P. syringae* pv. tomato DC3000 contains genes sufficient for coronamic acid biosynthesis. The cma gene cluster is also capable of converting valine into norcoronamic acid and isoleucine into diastereomer(s) of natural coronamic acid. Couch, R. et al. (2004) *J. Bacteriol.* 186: 35-42; Parry, R. J. et al. (1994) *J. Am. Chem. Soc.* 223: 1849-1850. Five genes (cmaA, cmaB, cmaC, cmaD and cmaE) are reported to be required for CMA and nCMA biosynthesis in vitro. Vaillancourt, F. H. et al. (2005) *Nature* 436: 1191-1194. An additional gene, cmaT, has thioesterase activity and is reported to be involved in the release of CMA from CmaD protein. Patel et al., (1998) Tetrahedron 54:15927-15936. Nucleotide and amino acid sequences for genes in cma gene clusters are disclosed under GenBank accession number AY381839 (gi: 37575137) and U14657 (gi: 2673889). Sequences for the cma gene cluster from *P. syringae* pv. tomato DC3000 can be found in the complete genomic sequence for this organism, under GenBank accession number AE016853 (gi: 28856110).

Synthesis of these cyclopropyl amino acids is reported to be controlled at the transcriptional level by trans-acting factors. For example, synthesis of cyclopropyl amino acids in *P. syringae* pv. *glycinea* PG4180 is reportedly regulated by a two-component system controlled by growth temperature. Bender et al, *Microbiol Mol Biol Rev* 63:266-292 (1999). Similarly, a negative transcription regulator, HrpV, has been reported to be involved in the synthesis of coronatine in *P. syringae* pv. tomato DC3000. Penaloza-Vazquez A, et al, *Microbiology* 146:2447-2456 (2000). HrpV negatively regulates expression of the hrp regulon. Deletion of this gene along with hrcC, and hrpT was found to increase synthesis of cyclopropyl amino acids by 30-40 fold. See, US 2007/0264691. All three genes (hrcC, hrpT and hrpV) are clustered together in *P. syringae* pv. tomato DC3000.

Expression of genes involved in the CMA and nCMA biosynthetic pathway (e.g., a cma gene cluster) in a microorganism confers the ability to synthesize coronamic acid or norcoronamic acid upon that microorganism. As discussed in more detail below, coronamic acid biosynthesis genes may be present naturally in a microorganism, e.g., *Pseudomonas*. In some cases, one or more such genes are recombinant genes that have been transformed into a microorganism that does not naturally possess them, e.g., *Escherichia coli, Saccharomyces cerevisiae, Synechocystis* 6803, *Synechococcus* 7002, *Methylomonas methanica, Methylococcus capsulatus,* or *Rhodopseudomonas palustris*.

CmaA is an amino acid adenylating enzyme that reacts with the AMP derivative of L-allo-isoleucine to produce an aminoacyl thiolester intermediate. CmaA contains adenylation and thiolation domains. Various cmaA sequences can be found under the following GenBank accession numbers: ZP_06482567 (gi: 289651224), ZP_07252114 (gi: 302060573), NP_794453 (gi: 28871834) and AAC46032 (gi: 2673890).

CmaB is a component of coronamic acid synthetase, a non-heme iron binding dioxygenase. Various cmaB sequences can be found under the following GenBank accession numbers: NP_794454 (gi: 28871835), ZP_06460771

(gi: 289627817) and ZP_04586949 (gi: 237798488) and YP_003450258 (gi: 288959918).

CmaC is a cyclase that catalyzes the formation of a cyclopropyl ring from chlorinated L-allo-isoleucine. Various cmaC sequences can be found under the following GenBank accession numbers: NP_794455 (gi: 28871836), ZP_07234588 (gi: 301386170), and ZP_06460770 (gi: 289627816) and YP_003450259 (gi: 288959919).

CmaE is an acetyltransferase that transfers amino acid groups between thiolation domains of CmaA and CmaD. Various cmaE sequences can be found under the following GenBank accession numbers: NP_794452 (gi: 28871833), ZP_06460773 (gi: 289627819), ZP_06482566 (gi: 289651223), ZP_07252113 (gi: 302060572), ZP_07235048 (gi: 301386630), ZP_04586951 (gi: 237798490) and AAO58147 (gi: 28855086).

CmaD is acyl carrier protein that has a phospho-pantetheine attachment site. Various cmaD sequences can be found under the following GenBank accession numbers: NP_794451 (gi: 28871832), ZP_04586952 (gi: 237798491), AAO58146 (gi: 28855085), ZP_06460774 (gi: 289627820), ZP_06482565 (gi: 289651222), ZP_07234760 (gi: 301386342), ZP_07252112 (gi: 302060571).

CmaT is a thioesterase component involved with coronamic acid synthetase in the release of CMA from CmaD protein. Various cmaT sequences can be found under the following GenBank accession numbers: NP_794456 (gi: 28871837), ZP_06482572 (gi: 289651229), ZP_07234587 (gi: 301386169), ZP_06460769 (gi: 289627815) and ZP_04586947 (gi: 237798486).

In view of the above, it will be appreciated that recombinant genes for the six coronamic acid biosynthesis polypeptides described above need not necessarily be from a naturally occurring cma gene cluster. Instead, a useful combination of genes can be constructed using genes from different species or from different strains of the same species. Thus, one or more nucleic acid constructs useful in the invention can have genes encoding coronamic acid biosynthesis polypeptides that are derived from or are functional homologs of genes from the same strain, from two different species or strains, three different species or strains, four different species or strains, five different species or strains, or even six different species or strains.

Functional homologs of the CMA and nCMA biosynthesis polypeptides described above are also suitable for use in alkene production in a recombinant microorganism. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a polypeptide, or by combining domains from the coding sequences for different naturally-occurring polypeptides ("domain swapping"). Functional homologs can also be created via site-directed mutagenesis of the coding sequence for a naturally occurring polypeptide, or by combining domains from the coding sequences for different naturally-occurring polypeptides ("domain swapping"). Techniques for modifying genes encoding functional coronamic acid biosynthesis polypeptides and ACC oxidases described herein are known and include, inter alia, directed evolution techniques, site-directed mutagenesis techniques and random mutagenesis techniques, and can be useful to increase specific activity of a polypeptide, alter substrate specificity, alter expression levels, alter subcellular location, or modify polypeptide: polypeptide interactions in a desired manner. Such modified polypeptides are considered functional homologs. The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of coronamic acid biosynthesis polypeptides. Sequence analysis can involve BLAST, Reciprocal BLAST, or PSI-BLAST analysis of nonredundant databases using a coronamic acid biosynthesis polypeptide amino acid sequence as the reference sequence. Amino acid sequence is, in some instances, deduced from the nucleotide sequence. Those polypeptides in the database that have greater than 40% sequence identity are candidates for further evaluation for suitability as a coronamic acid biosynthesis polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in coronamic acid biosynthesis polypeptides, e.g., conserved functional domains.

Conserved regions can be identified by locating a region within the primary amino acid sequence of a CMA and nCMA biosynthesis polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity. It will be appreciated that functional homologs of the polypeptides described below are also suitable for use in alkene production in a recombinant microorganism.

ACC Oxidase Polypeptides 1-aminocyclopropane-1-carboxylate oxidase (ACC oxidase) is an enzyme naturally found in plants, and a member of a superfamily of non-heme iron oxygenases and oxidases.

ACC oxidase cleaves two carbon-carbon bonds in 1-aminocyclopropane-1-carboxylate (ACC) to produce ethylene, cyanide, and $CO_2$. The enzyme uses ascorbate as a co-substrate, in contrast to most non-heme iron oxygenases and oxidases, which use 2-ketoglutarate. $CO_2$ also acts as an activator of ACC oxidase in many cases, unlike other members of the non-heme enzyme superfamily. ACC oxidase is encoded by a multigene family in most plant species. For example, the *Arabidopsis* genome encodes five ACC oxidase genes, while tomato encodes six. See Lin, Z et al., supra, and Blume, B. and Grierson, D. *Plant J.* 12: 731-746 (1997).

It has been discovered that ACC oxidase can not only utilize ACC as a substrate, it can also utilize coronamic acid, yielding 1-butene as the reaction product. Furthermore, ACC oxidase can utilize norcoronamic acid as a substrate, yielding propene as the reaction product. All diastereoisomers of coronamic acid and norcoronamic acid (1R,2R; 1R,2S; 1S,2R; 1S,2S) are oxidized by ACC oxidase. Thus, expression in a recombinant microorganism of coronamic acid biosynthesis pathway genes and an ACC oxidase gene results in the conversion of isoleucine to 1-butene. Furthermore, expression in a recombinant microorganism of coronamic acid biosynthesis pathway genes and an ACC oxidase gene results in the conversion of valine to propene.

By-Product Recycling Polypeptides

Butene and/or propene synthesis in a recombinant microorganism generates $CO_2$ and CN as by-products. While $CO_2$ is lost as a gas or recaptured in the case of photosynthetic organisms, CN is toxic to many microorganisms. Therefore, the presence of a cyanide detoxification pathway in the recombinant microorganism can facilitate higher throughput and increased alkene yield during culture and provide a mechanism to capture reduced carbon and nitrogen efficiently. Enzymes suitable for use in cyanide detoxification include β-cyanoalanine synthase and nitrilase. Co-expression of a β-cyanoalanine synthase and a nitrilase converts cyanide to a moiety in asparagine, which can then be converted into various other amino acids. Thus, the combination of β-cyanoalanine synthase and nitrilase not only detoxifies the cyanide by-product, it can also recycle nitrogen from coronamic acid into the amino acid pool, thereby reducing the amount of nitrogen required in culture media when producing alkenes.

Genes encoding β-cyanoalanine synthases are known. Several plant species have efficient β-cyanoalanine synthases for detoxifying cyanide. Genes for nitrilases can be found in a wide range of mesophilic microorganisms, including species of *Bacillus, Norcardia, Bacteridium, Rhodococcus, Micrococcus, Brevibacterium, Alcaligenes, Acinetobacter, Corynebacterium, Fusarium* and *Klebsiella*.

Other Polypeptides

Genes for additional polypeptides that facilitate more efficient or larger scale production of a desired alkene can also be introduced into a recombinant microorganism.

For example, a recombinant microorganism can also contain a gene encoding a threonine dehydratase or a gene encoding a homoserine dehydratase. Such genes are useful because they can increase the flux of carbon and nitrogen into the isoleucine pathway, producing 2-keto butyrate from the homoserine generated by the cyanide detoxification pathway. The ammonia released can be captured by including a gene encoding an alanine dehydrogenase or a gene encoding a glutamate dehydrogenase.

In some embodiments, a recombinant microorganism also contains a gene encoding GDP mannose synthase, GDP D-mannose epimerase, GDP L-galactose pyrophosphorylase, L-galactose dehydrogenase, and L-galanolactone dehydrogenase. This group of genes function together to produce ascorbate biosynthetically. Other pathways are also available for increasing the flux of carbon through ascorbate, an important cosubstrate for ACC oxidase.

In some embodiments, a recombinant microorganism can also contain a gene encoding a serine O-acetyl transferase. This enzyme catalyzes one of the steps in the biosynthesis of L-cysteine, the predominant way by which inorganic sulphur is incorporated into organic compounds. Serine O-acetyl transferase is able to catalyze the reaction of acetyl-coenzyme A and L-serine to produce coenzyme A and O-acetyl-L-serine.

Valine and Isoleucine Biosynthesis

The flux through the native biosynthetic pathway genes for valine and/or isoleucine biosynthesis in a recombinant microorganisms is often sufficient to produce butene and/or propene as described herein. However, it is useful in some instances, to modify endogenous genes in a recombinant microorganism in order to increase the rate at which valine and/or isoleucine are synthesized. Such modifications include point mutations, insertions, deletions and genome rearrangements, and can be accomplished by, e.g., directed evolution techniques.

In other instances, it is useful to further increase flux through the valine or isoleucine biosynthesis pathways by introducing one or more recombinant genes encoding and expressing polypeptides involved in valine biosynthesis into a recombinant microorganism. For example, a recombinant microorganism can contain one or more of the following recombinant genes: a gene encoding an acetohydroxyacid synthase II insensitive to feedback inhibition by valine, a gene encoding an acetohydroxyacid reductoisomerase, a gene encoding a dihydroxyacid dehydratase and a gene encoding a transaminase-B. Elišáková et al. (2005) *Applied and Environ, Microbiol.*, 71: 207-213. Expression of such genes in the microorganism can result in an increase in the amount of valine produced, compared to a corresponding microorganism that lacks such recombinant genes. In some embodiments, a recombinant gene encoding a valine-isoleucine transaminase that exhibits a preference for L-allo-isoleucine can be introduced into a recombinant microorganism and thereby increase in the amount of L-allo-isoleucine produced, compared to a corresponding microorganism that lacks such a recombinant gene.

A recombinant microorganism can also contain genes encoding and expressing polypeptides involved in isoleucine biosynthesis and, in some instance, isomerization of L-isoleucine to L-allo-isoleucine. There are two known pathways for isoleucine biosynthesis, which differ from each other in the manner in which 2-ketobutyrate is synthesized. Some microorganisms synthesize 2-ketobutyrate from threonine by threonine deaminase. Other microorganisms synthesize 2-ketobutyrate from citramalate via condensation of acetyl-CoA and pyruvate using a series of enzymatic reactions, including citramalate synthase and isopropyl malate dehydrogenase. Atsumi S, et al., *Appl Environ Microbiol* 74:7802-7808 (2008). 2-ketobutyrate is then converted to isoleucine in four enzymatic steps. Polypeptides involved in the common portion of the isoleucine biosynthesis pathway, or in one or both of the 2-ketobutyrate portions of the isoleucine biosynthesis pathway, can be introduced via recombinant genes encoding the desired polypeptide(s) and thereby increase in the amount of valine produced, compared to a corresponding microorganism that lacks such recombinant genes. Polypeptides involved in isomerization of L-isoleucine to L-allo-isoleucine can also be introduced as recombinant genes, if desired. In some embodiments, a recombinant gene encoding pyridoxal phosphate aminotransferase is introduced into a microorganism. Pyridoxal phosphate aminotransferase has been reported to catalyze the formation of L-allo-isoleucine from L-isoleucine. Mamer J. Chromatography 758: 49-55 (2001).

For those microorganisms for which 2-ketobutyrate is mainly synthesized from threonine, deregulation of threonine deaminase can achieve greater amounts of isoleucine. For example, a recombinant microorganism can contain a gene encoding a threonine deaminase and a gene encoding an aspartate kinase that is insensitive to feedback regulation by threonine. Feedback-insensitive mutant aspartate kinases are known, e.g., feedback-insensitive *E. coli* aspartate kinases, and can result in increased levels of the substrate threonine. As another example, a recombinant microorganism can contain one or more of the following recombinant genes: a gene encoding a feedback-insensitive aspartate kinase, a gene encoding a threonine deaminase resistant to feedback inhibition by isoleucine, a gene encoding an acetohydroxyacid synthase II insensitive to feedback inhibition by isoleucine, a gene encoding a acetohydroxyacid reductoisomerase (EC 1.1.1.86), a gene encoding a dihydroxyacid dehydratase (EC 4.2.1.9) and a gene encoding a transaminase-B (EC 2.6.1.42). Expression of one or more of such genes results in an increase in the amount of isoleucine compared to a corresponding microorganism that lacks such recombinant genes.

In some embodiments, a recombinant microorganism contains one or more of the following recombinant genes: a gene encoding a citramalate synthase, a gene encoding an acetohydroxyacid synthase II insensitive to feedback inhibition by isoleucine, a gene encoding an acetohydroxyacid reductoisomerase, a gene encoding a dihydroxyacid dehydratase and a gene encoding a transaminase-B. Expression of one or more of such genes results in an increase in the amount of isoleucine compared to a corresponding microorganism that lacks such recombinant genes.

Some microorganisms, such as *P. syringae* pv. tomato DC3000, contain genes for threonine deaminase as well as genes involved in the citramalate pathway, indicating that 2-ketobutyrate may be produced either from threonine or directly from pyruvate for these microorganisms. Therefore, the flux through one or both of the threonine deaminase portion or the citramalate portion of the isoleucine pathway can be modified in such microorganisms in order to increase amount and rate of isoleucine biosynthesis.

Redox Polypeptides

It can be useful to balance redox metabolism in a recombinant microorganism, specifically, the steady state level of NADPH. To achieve balanced redox metabolism, a recombinant gene encoding a glyceraldehyde-3-phosphate dehydrogenase that uses NADP-NADPH rather than NAD-NADH can be expressed to accumulate NADPH. An example of such an enzyme is a glyceraldehyde-3-phosphate dehydrogenase from *Clostridium acetobutylicum*. As another example, a recombinant gene encoding a functional NAD(P)+transhydrogenase can be expressed in the microorganism. Soluble transhydrogenases are particularly useful in this regard.

Genes

A gene encoding a polypeptide described herein comprises the coding sequence for that polypeptide, operably linked in sense orientation to one or more regulatory regions suitable for expressing the polypeptide. Because many microorganisms are known to encode multiple proteins of a pathway in a polycistronic unit, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof A regulatory region typically comprises at least a core (basal) promoter. A regulatory region also may include at least one control element, such as an enhancer sequence, an upstream element or an upstream activation region (UAR).

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., introns, enhancers, upstream activation regions, transcription terminators, and inducible elements.

It will be appreciated that it may be desirable to remove certain regulatory regions in order to increase expression levels. For example, it may be desirable to remove attenuator regions to increase the expression of valine biosynthesis polypeptides. See, Hashiguchi K et al., *Biosci Biotechnol Biochem* 63:672-679 (1999).

One or more genes can be combined in a recombinant nucleic acid construct in "modules" useful for a discrete aspect of alkene production. Combining a plurality of genes in a module, particularly a polycistronic module, facilitates the use of the module in a variety of species. For example, a cma gene cluster and an ACC oxidase can be combined in a polycistronic module such that, after insertion of a suitable regulatory region, the module can be introduced into a wide variety of non-Pseudomonas species. In addition to genes useful for alkene production, a recombinant construct typically also contains an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular microorganism is obtained, using appropriate codon bias tables for that microorganism, and codon-optimized nucleic acids are typically used when the polypeptide to be expressed is heterologous for that microorganism. See FIG. 2, which shows an ACC oxidase coding sequence optimized for expression in *Pseudomonas*.

In some cases, it is desirable to inhibit one or more functions of an endogenous polypeptide of an endogenous polypeptide. For example, it may be desirable to inhibit coronafacic acid biosynthesis in a *Pseudomonas* strain using recombinant techniques. In such cases, a nucleic acid that inhibits expression of a protein involved in coronafacic acid biosynthesis may be included in a recombinant construct that is then transformed into the strain.

Microorganisms

A number of prokaryotes and eukaryotes are suitable for use in constructing the recombinant microorganisms described herein, e.g., Gram-negative bacteria, yeast and fungi. Typically, a species and strain selected for development as an alkene production strain is first analysed to determine which alkene production genes are endogenous to the strain and which genes are not present. Genes for which an endogenous counterpart is not present in the strain are assembled in one or more recombinant constructs, which are then transformed into the strain in order to supply the missing function(s). Genes for which an endogenous counterpart is present in the strain can, if desired, be modified as described above or supplemented with one or more recombinant genes in order to enhance flux in the strain through particular pathways or particular steps.

Exemplary prokaryotic and eukaryotic species are described in more detail below. However, it will be appreciated that other species may be suitable. For example, suitable species may be in a genus selected from the group consisting of *Acetobacter, Achromobacter, Acidiphilium, Acinetobacter, Alcaligenes, Bacillus, Bifidobacterium, Brevibacillus, Clostridium, Corynebacterium, Escherichia, Enterococcus, Erwinia, Klebsiella, Kluyveromyces, Lactobacillus, Leuconostoc, Methanogenium, Methylomonas, Micrococcus, Propionibacterium, Pseudomonas, Pyrococcus, Streptococcus, Streptomyces, Trichoderma, Xanthomonas*, and *Zymomonas*. In some embodiments, a microorganism can be a cyanobacterium selected from the group consisting of *Synechocystis, Synechococcus, Anabaena, Cyanothece, Thermosynechococcus, Rhodopseudomonas*. In some embodiments, a microorganism of a genus selected from the group consisting of *Aspergillus, Candida, Pichia, Saccharomyces*, and *Rhodotorula*. In some embodiments, a microorganism can be a photosynthetic microorganism. For example, the organism can be of a genus selected from the group consisting of *Chlamydomonas, Dunaliella, Chlorella, Botryococcus, Nannochloropsis, Physcomitrella*, and *Ceratodon*.

Pseudomonas

A recombinant microorganism, as provided herein can be a *Pseudomonas* species, particularly *P. syringae*. *P. syringae* is a natural coronamic acid producer, and therefore production of 1-butene by *P. syringae* can be achieved by insertion of a single gene, a gene encoding an ACC oxidase. Many strains of *P. syringae* are available, as well as, mutants in various genes. A number of plasmids are available preparing recombinant constructs that contain desired genes. Transformation methods are known by which constructs can be introduced into *P. syringae* and make a recombinant microorganism.

The native coronatine biosynthesis pathway in *P. syringae* involves production of coronamic acid and a second precursor to coronatine, coronafacic acid. In the presence of coronafacic acid, coronatine synthase can compete with ACC oxidase for coronamic acid and thereby reduce the amount of butene that would otherwise be produced. Accordingly, a null mutation in a coronafacic acid pathway gene can be used to prevent formation of coronafacic acid. *P. syringae* strains containing coronafacic acid mutations are known. See, e.g., Brooks, D. M. et al. (2004) Mol. Plant. Microbe. Interact. 17:162-174. Alternatively, a recombinant construct that includes a gene inhibiting production of coronafacic acid can be introduced. In another embodiment, coronafacic acid synthesis can be inhibited through the use of a culture medium comprising an inhibitor of coronafacic acid biosynthesis.

In one embodiment, a tomato ACC oxidase is introduced in *P. syringae*. This isoform has previously been expressed and purified in active form from *E. coli*, and thus is expected to be active in *Pseudomonas*, although ACC oxidases from other species can also be used. Cyanide detoxification pathway genes such as β-cyanoalanine synthase and nitrilase are also introduced. Other optional genes can be introduced in the selected *Pseudomonas* strain, as discussed above.

*Escherichia coli*

*Escherichia coli*, a widely used chassis organism in synthetic biology, can also be used as the recombinant microorganism platform. There are libraries of mutants, plasmids, detailed computer models of metabolism and other information available for *E. coli*, allowing for rational design of various modules to enhance product yield. Methods similar to those described above for *P. syringae* can be used to make recombinant *E. coli* microorganisms.

There are a number of broad host range plasmids from different sources that can be used to facilitate gene cloning and expression in *P. syringae* and *E. coli*. Some of the plasmids are pBBR1MCS2, pBBR1MCS3, pBBR1MCS4, pBBR1MCS5 and pBBR1MCS8; pMEKm12; pME6031; pSL1211; pJRDlacI; pLAH30, pLAH31 and pLAH32. Kovach M E, et al. *Gene* 166:175-176 (1995); Lu S E, et al., *FEMS Microbiol Lett* 210:115-121 (2002); Mellgren E M, et al., *J Bacteriol* 191:3132-3141 (2009); Ng W O, et al., *Arch Microbiol* 173:412-417 (2000); Bertani I, et al., *FEMS Microbiol Lett* 179:101-106 (1999). These plasmids harbor different origins of replication and different antibiotic markers, allowing multiple plasmids to be transferred simultaneously in *P. syringae* and *E. coli* strains. *E. coli* promoters such as the trc, tac and lacUV5 promoters are active in *P. syringae* strains.

For *E. coli*, coronamic acid biosynthesis genes and an ACC oxidase gene can be inserted in a plasmid such that expression is controlled by suitable inducible promoters. For example, promoters whose expression is tightly controlled by sugars such as arabinose can be used. Once constructed, the expression plasmid is introduced into a suitable *E. coli* strain. Strains that overproduce isoleucine and valine are known and can be used as recipients of such an expression plasmid, in order to further increase the production of butene and/or propene. Park, J. H., et al. (2007) Proc. Natl. Acad. Sci. 104: 7797-7802 and Hashiguchi, K. et al. (1999) Biosci. Biotechnol. Biochem. 63: 672-679.

In some embodiments, coronamic acid biosynthesis genes are expressed on a plasmid under the control of a constitutive promoter and an ACC oxidase gene is expressed under the control of an inducible promoter. Once constructed, the expression plasmid is introduced into a suitable *E. coli* strain, and coronamic acid or norcoronamic acid are converted into 1-butene and propene, respectively, when the ACC oxidase is induced. Genes for cyanide detoxification are included as described above.

*Saccharomyces cerevisiae*

*Saccharomyces cerevisiae* is another widely used chassis organism in synthetic biology, and can also be used as the recombinant microorganism platform. Similar to *E. coli* and *Pseudomonas*, there are libraries of mutants, plasmids, detailed computer models of metabolism and other information available for *S. cerevisiae*, allowing for rational design of various modules to enhance product yield. Methods are known for making recombinant microorganisms.

Coronamic acid biosynthesis genes and an ACC oxidase gene can be expressed in yeast using any of a number of known promoters. Genes for cyanide detoxification are included as described above. Strains that overproduce threonine are known and can be used to increase the amount of isoleucine available for alkene production.

*Synechocystis*

*Synechocystis* 6803 can be used as the chassis for a recombinant microorganism. *Synechocystis* is a well-characterized cyanobacterium and its genome has been sequenced. It can utilize a wide variety of energy and carbon sources, including, sugars, $CO_2$, and sunlight. A large collection of knock-out mutants are available, along with the largest cyanobacterial genome-level transcriptomic (more than 160 conditions) and proteomic (more than 35 conditions) datasets.

In the mixotrophic mode, *Synechocystis* 6803 can grow at rates exceeding the sum of autotrophic and heterotrophic growth rates. This contrasts with many microbes capable of mixotrophic growth, where providing fixed carbon strongly decreases $CO_2$ fixation. This makes *Synechocystis* a suitable species for combining energy sources for the conversion of fixed carbon and $CO_2$ into alkenes. In addition, the mixotrophic capability of *Synechocystis* can allow it to recapture $CO_2$ lost during coronamic acid/norcoronamic acid oxidation, boosting its carbon efficiency over heterotrophic organisms.

Coronamic acid biosynthesis genes operably linked to suitable promoters, e.g., the controllable lacUV5 promoter, and an ACC oxidase operably linked to a constitutive promoter can be introduced into this microorganism to allow alkene production. An advantage of *Synechocystis* 6803 is that it contains endogenous genes that function to degrade HCN to $CO_2$ and $NH_3$. Thus, cyanide detoxification genes are not required for this species. In some embodiments, genes that enhance recycling of $CO_2$ and $NH_3$, such as alanine dehydrogenase or glutamate dehydrogenase, can be introduced.

*Synechocystis* 6803 can be modified for overproduction of isoleucine and/or valine. See, e.g., Atsumi, S., Higashide, W., and Liao, J. C. (2009) *Nat. Biotech.* 27: 1177-8.

Other cyanobacterial strains with important functional attributes can also be used as the chassis for a recombinant microorganism. For example, *Synechococcus* 7002 is a marine unicellular cyanobacterium that has several unique features suitable for alkene production. This strain is one of the fastest growing cyanobacteria and has ability to tolerate high intensities of light and, in addition to $CO_2$ and sunlight, it can utilize glycerol for growth. Its genome has been sequenced, and genetic manipulation including gene modification, insertion and deletion is routinely performed.

As described above for *Synechocystis* 6803, coronamic acid biosynthesis genes and an ACC oxidase can be introduced into Synechococcus 7002 to allow alkene production.

*Rhodopseudomonas palustris*

*Rhodopseudomonas palustris* is a photosynthetic bacterium capable of growing in presence or absence of oxygen using a number of substrates. *R. palustris* possesses the capability for $H_2$ utilization. The *R. palustris* genome has been sequenced, and the organism is readily transformable. These organisms can be cultured on minimal media supplemented with $NaHCO_3$ and $H_2$ in the headspace, using sunlight and an uptake hydrogenase to generate reductant and drive $CO_2$ fixation via the Calvin cycle. Rey, F. E., et al. (2006) *J. Bacteriol.* 188(17):6143-52. Therefore, in some embodiments, this organism can be used to provide 'up-conversion' of electrical energy and waste $CO_2$ to liquid fuels.

Coronamic acid biosynthesis genes and an ACC oxidase gene, each operably linked to a constitutive promoter, can be inserted in an available plasmid and introduced into *R. palustris* to enable alkene production. Cyanide detoxification can be accomplished using genes described above for *Pseudomonas* and *E. coli*.

*Methylococcus capsulatus*

Microorganisms from the genera *Methylococcus* or *Methylomonas*, such as *Methylococcus capsulatus* Bath and *Methylomonas methanica*, can utilize methane either aerobically or anaerobically. These microorganisms can be cultured on nitrate mineral salts medium (NMS) supplemented with methane. See Whittenbury & Dalton, *The Prokaryotes*, pp. 894-902 (1981). For example, the microorganism can be cultured at 42° C. in a medium in which a methane source, e.g., a 1:1 (v/v) ratio of $CH_4$/air, is present in the headspace.

*Methylococcus capsulatus* Bath can also fix atmospheric nitrogen thus eliminating the requirement of fixed nitrogen source. See Murrel & Dalton (1983) *J Gen Microbiol* 129: 3481-3486. The microorganism can be cultured in the presence or absence of copper, e.g., 10 µM final concentration, which modulates the activity of the soluble versus insoluble forms of MMO. By regulating the concentration of nitrogen (nitrate or ammonia) and copper, one can regulate the activity and functionality of enzymes involved in methane metabolism. *Methylomonas* microorganisms typically contain a nitrite dismutase gene and express it under anaerobic conditions such that nitrite is converted to oxygen and nitrogen. The oxygen so produced is utilized by the microorganism to oxidize methane to methanol via methane monooxygenase (MMO). Coronamic acid biosynthesis genes (e.g., a cma gene cluster) and an ACC oxidase gene, each operably linked to a constitutive or an inducible promoter, can be introduced into such a microorganism and thereby enable alkene production from the branched chain amino acids.

Transformation systems for *Methylococcus capsulatus* Bath are known, e.g., Stolyar et al., Microbiology, 1999:145: 1235-1244. Expression systems including a series of integrative and broad-host-range vectors carrying suitable promoters have been shown to satisfactorily express genes from Gram-negative bacteria in *Methylococcus capsulatus* Bath, see Ali & Murrell, Microbiology, 2009:155:761-771 and can be used to express recombinant genes, e.g., coronamic acid biosynthesis genes and an ACC oxidase gene.

In some embodiments, cyanide detoxification genes described above for *Pseudomonas* and *E. coli* are also inserted into the recombinant Methylomonas microorganism. Typically, a recombinant *Methylomonas* microorganism also contains genes for ascorbate biosynthesis, e.g., genes encoding GDP mannose synthase, GDP D-mannose epimerase, GDP L-galactose pyrophosphorylase, L-galactose dehydrogenase, and L-galactonolactone dehydrogenase. In some embodiments, genes for valine and/or isoleucine biosynthesis as described above are also introduced.

Methods of Producing Alkenes

Recombinant microorganisms described herein can be used in a method to produce alkenes such as 1-butene and propene. The method includes growing the recombinant microorganism in a culture medium under conditions in which coronamic acid biosynthesis genes and an ACC oxidase gene are expressed. Depending on the particular microorganism used in the method, other recombinant genes such as cyanide detoxification pathway genes may also be present and are expressed. The amount of alkene produced during growth in culture can be monitored if desired, by extracting gas from the headspace of the cultures and analyzing the samples via GC-MS, according to published methods. Zhang et al. *Biochem J* 307:77-85 (1995). Levels of substrates and intermediates, e.g., coronamic acid, norcoronamic acid, isoleucine and valine, can be determined by extracting samples from culture media for analysis via TLC and HPLC according to published methods. Ullrich, M. and Bender, C. L. (1994) *J. Bacteriol.* 176: 7574-7586.

After the recombinant microorganism has been grown in culture for the desired period of time, 1-butene and/or propene can then be recovered from the fermentor using various methods known in the art. Butene and propene have low water solubility, high vapor pressure and readily volatilize from the culture medium. Accordingly, butene or propene can be collected as a volatile from the gaseous components in the fermentor. Membrane separators can be used to recover alkenes from other gaseous components. Since butene and propene condense at relatively low pressure (~500 psi), they can be liquified from the bulk gas stream from the fermentor and thereby separated from the remainder of the gaseous components. Production of alkenes such as 1-butene and propene by recombinant microorganisms as described herein avoids some of the costly, energy-intensive methods of producing butene and propene.

Linear and branched chain alkenes produced by the recombinant microorganisms described herein, containing one or more double bonds, have significant utility in view of the functionality provided by such bonds. The 1-butene or propene obtained by the methods disclosed herein can then be subjected to various types of catalytic reactions to form liquid fuels such as alkanes and alcohols. For example, butene can be oligomerized to produce octane, dodecene, or hexadecane. Butene can also be used to make materials and chemical intermediates such as polybutylene, polyethylene and propylene mixtures, butadiene, or butyl rubber.

It will be appreciated that the various genes and modules discussed herein can be present in two or more recombinant microorganisms rather than a single microorganism. When a plurality of recombinant microorganisms is used, they can be grown in a mixed culture to produce alkenes. For example, a first microorganism can comprise one or more coronamic acid biosynthesis genes while a second microorganism comprises a gene encoding an ACC oxidase, a gene encoding a β-cyanoalanine synthase, and a gene encoding a nitrilase. Alternatively, the two or more microorganisms are each grown in a separate culture medium and the product of the first culture medium, e.g., coronamic acid, is introduced into second culture medium to be converted into a subsequent intermediate, or into the end product alkene. In another example, a first organism can be a specialized microorganism that utilizes one or more substrates such as $CO_2$, $CH_4$, $H_2$ and excretes sugar or reduced carbon molecules. The excreted sugar or reduced carbon molecules are then utilized by second recombinant microorganism to produce 1-butene and/or propene.

When methane, $H_2$ or other volatile substrate compounds are used as part of the culture conditions, the recombinant microorganism is grown in a culture medium under conditions in which coronamic acid biosynthesis genes and an ACC oxidase gene are expressed, and the volatile substrate(s) is introduced into the culture, typically by bubbling into the liquid medium. The alkene product(s), e.g., 1-butene and/or propene, can be recovered from the headspace as a volatile through the use of a series of molecular sieves or other methods known in the art to fractionate butene and/or propene in high purity from offgas. These separation methods permit separation of the alkene products from volatile components of the culture media.

The invention will be further described in the following examples, which do not limit the scope of the invention described in the claims.

EXAMPLES

Example 1

Pseudomonas Strains

*P. syringae* pv. tomato DC3000 is described in Cuppels, *Appl. Environ. Microbiol.* 52: 323-327 (1986). Strain DC3000 is a wild-type, pathogenic strain designated herein as MGC0001. In addition to the wild type strain MGC0001, DC3000 mutant strain DB4G3, which contains a Tn5 insertion in the cfa6 locus, was utilized. Brooks et al. *Mol. Plant. Microbe Inter.* 17: 162-174 (2004). DB4G3 is deficient in coronafacic acid and coronatine biosynthesis, and accumulates cyclic amino acids. Strain DB4G3 is designated herein as MGC0003.

Other mutant strains of *P. syringae* pv. tomato DC3000 include AK6F3 and AK7E2. Brooks et al., supra. AK6F3 contains a Tn5 insertion immediately upstream of the start codon for the first ORF in the CMA biosynthetic gene cluster, and produces small amounts of coronafacic acid and undetectable levels of coronatine. AK7E2 contains a Tn5 insertion in the cmaA gene, and produces small amounts of coronatine and slightly larger amounts of coronafacic acid. AK6F3 is designated herein as MGC0005 and AK7E2 is designated herein as MGC0006.

*P. syringae* pv. *glycinea* PG4180 is described in Bender et al., *Gene* 133:31-38 (1993). Strain PG4180 is a wild-type, pathogenic strain designated herein as MGC0002. In addition to the wild type strain MGC0002, PG4180 mutant strain A1 was utilized. Strain A1 contains a Tn5 insertion in the cfa6 gene, and is deficient in coronafacic acid and coronatine biosynthesis. Rangaswamy et al., *Proc Natl Acad Sci USA* 95: 15469-15474 (1998). *Pseudomonas* strains are listed in Table 1.

TABLE 1

*Pseudomonas* Strains

| Pathovar | Strain Designation | Recombinant Plasmid | Mutation(s) | Comments |
| --- | --- | --- | --- | --- |
| tomato DC3000 | MGC0001 | — | — | Wild type strain |
| glycinea PG4180 | MGC0002 | — | — | Wild type strain |
| tomato DC3000, strain DB4G3 | MGC0003 | — | cfa6 mutation | Deficient in coronafacic acid and coronatine synthesis |
| glycinea PG4180, strain A1 | MGC0004 | — | cfa6 mutation | Deficient in coronafacic acid and coronatine synthesis |
| tomato DC3000, strain AK6F3 | MGC0005 | — | first ORF of cma cluster | Deficient in coronamic acid and coronatine synthesis |
| tomato DC3000, strain AK7E2 | MGC0006 | — | cmaA mutation | Deficient in coronamic acid and coronatine synthesis |
| tomato DC3000 | MGC0007 | pBBR1MCS5_ACCO | — | |
| glycinea PG4180 | MGC0008 | pBBR1MCS5_ACCO | — | |
| tomato DC3000 | MGC0009 | pBBR1MCS5_ACCO | cfa6 mutation | |

TABLE 1-continued

Pseudomonas Strains

| Pathovar | Strain Designation | Recombinant Plasmid | Mutation(s) | Comments |
|---|---|---|---|---|
| glycinea PG4180, strain A1 | MGC0010 | pBBR1MCS5_ACCO | cfa6 mutation | |

Example 2

Microorganisms Expressing Codon-Optimized ACC Oxidase

A tomato ACC oxidase gene was codon optimized for expression in *P. syringae* pv. tomato DC3000, and synthesized at DNA 10 (Menlo Park, Calif. USA). The optimized gene shows 74% identity at the nucleotide level with the native ACC oxidase gene. An alignment of the native and codon-optimized nucleotide sequences is shown in FIG. 2. Two restriction sites (NdeI and KpnI) at either end of the gene were engineered to facilitate cloning.

For expression in *P. syringae* strains, the optimized gene was first cloned behind a lacUV5 promoter. The entire promoter-gene fragment was then cloned in the broad host range plasmid pBBR1MCS5 to generate a plasmid designated pBBR1MCS5_ACCO. pBBR1MCS5_ACCO was transferred into *Pseudomonas* strains by electroporation. To express ACC oxidase in *E. coli*, the optimized ACC oxidase gene was cloned in the pCOLADuet vector and expressed in BL21(DE3) cells.

Overnight cultures of strains of MGC0007 and *E. coli* carrying the recombinant plasmids with the optimized ACC oxidase gene were diluted in fresh LB medium (1% w/v Bacto-tryptone, 0.5% w/v Bacto-yeast extract and 1% w/v NaCl, pH 7.5) for *E. coli* and fresh NYG media (0.5% w/v Bacto-tryptone, 0.3% w/v Bacto-yeast extract and 2% v/v glycerol, pH 7.0) for *Pseudomonas*, and grown at the indicated temperature. Expression of ACC oxidase in *E. coli* was induced during log phase growth by the addition of 1 mM IPTG and incubating for 30 min. Expression of ACC oxidase in MGC0007 was measured on cells in the log phase of growth (about 2.5 hours after inoculation with an overnight culture). Total cellular extracts were prepared from the induced cells and fractionated by 12% protein gel electrophoresis as described by Zhang Z et al. *Biochem J* 307:77-85 (1995).

ACC oxidase activity was measured in the fractionated cell extracts as described by Zhang et al. Reaction mixtures including freshly prepared cellular extracts and ACC as substrate was transferred to an air-tight serum bottle. After incubation for 15 min at 30° C., 200 μl of the headspace was withdrawn with a syringe and analyzed by gas chromatography (Agilent). The results showed that ethylene was produced after expression of the codon-optimized ACC oxidase in *Pseudomonas*.

The in vitro method of Zhang et al. was modified to measure production of ethylene in intact cells of *E. coli* and *P. syringae*, by increasing the concentration of ascorbate and NAHCO₃ to 15 mM and removing the MOPS buffer. The amount of ethylene produced by intact cells was calculated by comparison to a standard curve generated from commercially available ethylene. The results showed that production of ethylene in *E. coli* and *P. syringae* was 1.14 and 0.08 nmoles/ml respectively, when grown at 30° C.

The in vivo and in vitro results establish that codon-optimized tomato ACC oxidase gene can be expressed and is functional in *P. syringae* and *E. coli*.

Example 3

Production of Propene and Butene by *P. syringae*

Recombinant microorganisms expressing the codon-optimized ACC oxidase of Example 2 were constructed in wild type and mutant strains of *P. syringae* pv. tomato DC3000 and *P. syringae* pv. *glycinea* PG4180. Specifically, strains MGC0001, MGC0002, MGC0003 and MGC0004 were transformed with pBBR1MCS5_ACCO to generate MGC0007, MGC0008, MGC0009 and MGC0010 strains, respectively. See, Table 1.

The strains were assayed for production of propene and butene by intact cells in culture. The initial results indicated that synthesis of propene and butene was lower when strains were grown in media containing yeast extract, bacterial peptone and glycerol, compared to synthesis of propene and butene when strains were grown in HSC media. Therefore all subsequent experiments were performed on cells grown in HSC media. HSC media is described in Palmer et al. *Appl Environ Microbiol* 1993, 59:1619-1626.

Figure 3:
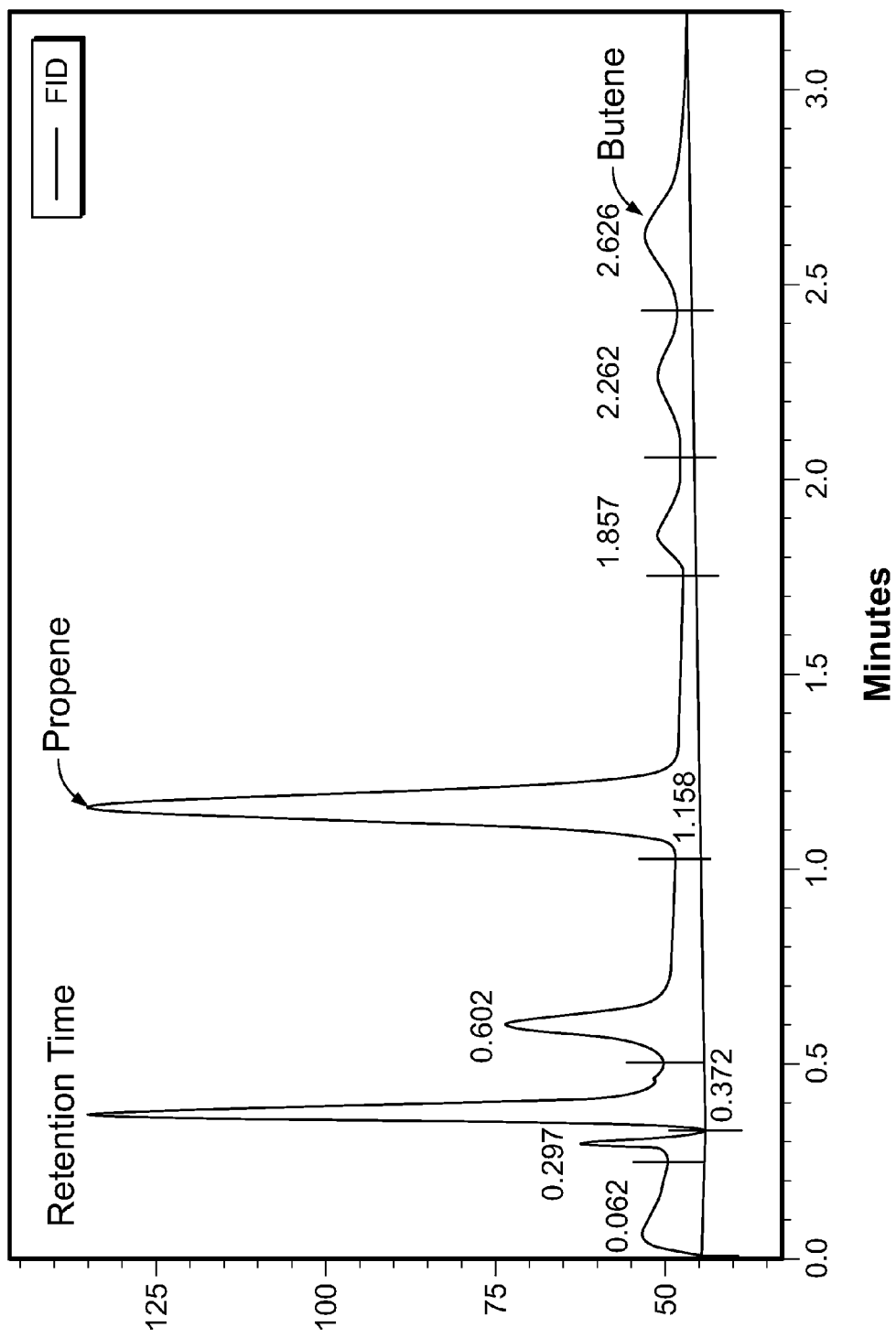
FIG. 3 shows a chromatographic trace of propene and butene production by recombinant *P. syringae* strains.

The synthesis of propene and butene by intact cells of *Pseudomonas* strains MGC0007, MGC0008, MGC0009 and MGC0010 was measured on cells grown in HSC media at 18° C. and 30° C. FIG. 3 is a representative trace of a gas chromatogram of volatile products in the headspace from cultures of intact cells. As shown in Table 2, the results indicate that the amounts of both propene and butene produced were greater when strains were grown at 18° C. relative to the amounts when grown at 30° C. In fact, no propene or butene could be detected when strain MGC0008 was grown at 30° C. The results also indicate that the amounts of propene and butene produced under these conditions were greater in strains MGC0009 and MGC0010 than in strains MGC007 and MGC008. These results suggest that strains MGC0009 and MGC0010 accumulate greater amounts of CMA and nCMA than do MGC007 and MGC008.

TABLE 2

Production of Propene and Butene by *Pseudomonas* Strains

| Strain | Growth temperature | Propene (nL/h/liter) | Butene (nL/h/liter) |
|---|---|---|---|
| MGC0007 | 30° C. | 17.3 | 7.3 |
| MGC0007 | 18° C. | 276.3 | 72.9 |
| MGC0008 | 30° C. | n.d. | n.d. |
| MGC0008 | 18° C. | 52.4 | 165.7 |
| MGC0009 | 30° C. | 236.4 | 67.7 |
| MGC0009 | 18° C. | 750.5 | 378.5 |
| MGC0010 | 30° C. | 41.3 | 13.6 |
| MGC0010 | 18° C. | 350.2 | 188.9 |

Example 4

Expression of a CMA Gene Cluster in Microorganisms

Genomic DNA from *P. syringae* pv. tomato DC3000 was isolated with a genomic DNA isolation kit and used as template for PCR amplification of cma gene clusters. PCR primers were designed to amplify the cmaD-C and cmaT-U clusters and the nucleotide sequences of the primers are shown in Table 3. Restriction sites (underlined) were introduced in the primers to facilitate cloning in the expression vectors.

TABLE 3

Primers for Amplification of cma Gene Clusters

| cma Cluster | Primer | Sequence |
|---|---|---|
| cmaD-C | Forward | CATATGAGCTCAGCAAAACTCGATC |
| cmaD-C | Reverse | CTCGAGTTAACCGGTGATCTCGAACAGG |
| cmaT-U | Forward | CCATGGCCGATCCTTTTGTGGTGC |
| cmaT-U | Reverse | GTCGACTAAAATGCCAATTTGGTCTTG |

The amplified products of each gene cluster are cloned into inducible expression plasmids for *E. coli, Synechocystis* and yeast. The level of expression of the CMA proteins is determined for each species under conditions in which expression from the plasmid is induced.

Example 5

Deletion of the hrp Gene Cluster in *P. syringae*

The plasmid pRK415 is used to construct mutant strains derived from *P. syringae* pv. tomato DC3000. Plasmid pRK415 is described in Alfano J R, et al, Proc Natl Acad Sci USA 2000, 97:4856-4861. The hrp gene cluster is deleted in MGC0009 by using double homologous recombination with pRK415 in the following manner. DNA fragments about 2 kb in length from both the upstream and downstream regions of the hrp gene clusters are PCR-amplified. An antibiotic cassette is introduced between the two clusters to facilitate selection of strains carrying both clusters. The newly created plasmid is then introduced into MGC0009 by electroporation and colonies growing in the presence of antibiotic are selected and confirmed for the deletion of the hrp gene cluster. Penaloza-Vazquez A, et al, *Microbiology* 146:2447-2456 (2000).

The resulting cfa6, hrp deletion strain is transformed with a plasmid carrying the following recombinant genes: a gene encoding an acetohydroxyacid synthase II insensitive to feedback inhibition by valine, a gene encoding an acetohydroxyacid reductoisomerase, a gene encoding a dihydroxyacid dehydratase and a gene encoding a transaminase-B. The resulting strain is grown in HSC media at 30° C. and the amount of valine synthesized is measured at different time periods. As controls, the amount of valine produced is compared to the amount synthesized by MG0009 and MG0001.

The resulting cfa6, hrp deletion strain is also transformed with a plasmid carrying the following recombinant genes: a gene encoding a feedback-insensitive aspartate kinase, a gene encoding a threonine deaminase resistant to feedback inhibition by isoleucine, a gene encoding an acetohydroxyacid synthase II insensitive to feedback inhibition by isoleucine, a gene encoding a acetohydroxyacid reductoisomerase, a gene encoding a dihydroxyacid dehydratase and a gene encoding a transaminase-B. The resulting strain is grown in HSC media at 30° C. and the amount of isoleucine synthesized is measured at different time periods. As controls, the amount of valine produced is compared to the amount synthesized by MG0009 and MG0001.

Other Embodiments

A number of embodiments of the invention have been described. Nevertheless, it will be understood that various modifications may be made without departing from the spirit and scope of the invention, which is defined by the scope of the appended claims. Other aspects, advantages, and modifications are within the scope of the following claims.

What is claimed is:

1. A recombinant prokaryotic microorganism of the genus *Pseudomonas*, comprising
   a) one or more coronamic acid biosynthesis genes whose expression results in production of coronamic and/or norcoronamic acid; and
   b) a gene encoding an 1-aminocyclopropane-1-carboxylic acid (ACC) oxidase, wherein at least one of said genes is a recombinant gene and said microorganism-produces 1-butene or propene.

2. The recombinant microorganism of claim 1, further comprising a gene encoding a β-cyanoalanine synthase and a gene encoding a nitrilase.

3. The recombinant microorganism of claim 1, wherein said one or more coronamic acid biosynthesis genes are an L-isoleucine or L-valine isomerase and a coronamic acid synthase.

4. The recombinant microorganism of claim 2, said microorganism further comprising a gene encoding an alanine dehydrogenase or a gene encoding a glutamate dehydrogenase.

5. The recombinant microorganism of claim 1, said microorganism further comprising a recombinant gene that inhibits production of coronafacic acid, or a null mutation in a coronafacic acid pathway gene.

6. The recombinant microorganism of claim 4, said microorganism further comprising a gene encoding a serine O-acetyl transferase.

7. The recombinant microorganism of claim 6, said microorganism further comprising genes encoding GDP mannose synthase, GDP D mannose epimerase, GDP L galactose pyrophosphorylase, L-galactose dehydrogenase and L-galanolactone dehydrogenase.

8. The recombinant microorganism of claim 7, said microorganism further comprising a gene encoding a threonine dehydratase or a gene encoding a homoserine dehydratase.

9. The recombinant microorganism of claim 8, said microorganism further comprising a gene encoding a feedback resistant acetohydroxyacid synthase.

10. The recombinant microorganism of claim 9, said microorganism further comprising a gene encoding a threonine deaminase, a gene encoding a citramalate synthase, or a gene encoding an isopropyl malate dehydrogenase.

11. A method of producing 1-butene or propene, comprising the steps of:
    a) growing the recombinant microorganism of claim 1 in a culture medium, under conditions in which said coronamic acid biosynthesis genes and said ACC oxidase gene are expressed; and
    b) recovering said 1-butene or propene produced by said microorganism.

12. The method of claim 11, wherein said 1-butene or propene is recovered as a volatile product from gaseous components in the fermentor.

13. The method of claim 11, wherein said culture medium comprises an inhibitor of coronafacic acid biosynthesis.

14. The method of claim 11, wherein said culture medium comprises a compound selected from the group consisting of glycerol, glucose, xylose, $CO_2$, $H_2$ and $CH_4$.

* * * * *

SEQUENCE LISTING

```
<160> NUMBER OF SEQ ID NOS: 6

<210> SEQ ID NO 1
<211> LENGTH: 956
<212> TYPE: DNA
<213> ORGANISM: Lycopersicon esculentum

<400> SEQUENCE: 1
catatggaga acttcccaat tattaacttg gaaaagctca atggagatga gagagccaac      60
catatggaga acttcccaat tattaacttg gaaaagctca atggagatga gagagccaac     120
ggaattccac atgaagtaat ggacacagta gagaaaatga caaagggaca ttacaagaag     180
tgcatggaac agaggtttaa ggaactagtg gcaagtaagg gacttgaggc tgttcaagct     240
gaggttactg atttagattg ggaaagcact ttcttcttgc gccatcttcc tacttctaat     300
atctctcaag tacccgatct tgacgaagaa tacagagagg tgatgagaga ttttgctaaa     360
atctctcaag tacccgatct tgacgaagaa tacagagagg tgatgagaga ttttgctaaa     420
aaaggttact tgaaaaatgc cttttatgga tcaaaaggtc ccaactttgg tactaaagtt     480
```

```
agcaactatc caccatgtcc taagcccgat tgatcaagg gactccgcgc tcatacagac    540
gcaggaggca tcatacttct gttccaagat gacaaagtga gtggccttca actcctcaaa    600
gacgagcaat ggatcgatgt tcctcccatg cgccactcta ttgtggttaa ccttggtgac    660
caacttgagg tgatcactaa cgggaagtac aagagtgtgc tgcacagagt aattgcacaa    720
acagacggga cacgaatgtc attagcctca ttttacaatc caggaagtga tgcagtaata    780
tatccagcaa aaactttggt tgaaaaagag gcagaggaaa gtacacaagt gtatccaaag    840
tttgtgtttg atgattacat gaagttatat gctggactca agtttcaagc caaagagcca    900
agatttgaag caatgaaggc aatggaaagt gatccaattg caagtgctta ggtacc         956
```

\<210\> SEQ ID NO 2
\<211\> LENGTH: 956
\<212\> TYPE: DNA
\<213\> ORGANISM: Artificial Sequence
\<220\> FEATURE:
\<223\> OTHER INFORMATION: Synethetic coding sequence

\<400\> SEQUENCE: 2

```
catatggaga acttcccgat catcaatctg gagaaactga acggcgacga acgcgcgaac    60
accatggaaa tgattaagga tgcatgcgag aattgggggtt tcttcgaact ggtcaatcat    120
ggtatcccgc acgaggtgat ggatacggtt gagaagatga ccaagggcca ctacaaaaag    180
tgtatggaac agcgctttaa agagctggtg gcgagcaaag gtctggaagc ggtccaagct    240
gaagtgacgg atttggactg ggagtccacc ttctttctgc gtcatttgcc gaccagcaac    300
attagccaag ttccggatct ggatgaagaa taccgtgagg tcatgcgtga ctttgcgaag    360
cgtctggaga gttggcaga agagctgctg gatctgctgt gcgagaacct gggcttggag    420
aagggttatc tgaagaacgc cttctatggc agcaagggtc cgaatttcgg tacgaaggtg    480
tctaactatc cgccgtgtcc taaaccggac ctgattaagg gtttgcgtgc acacaccgat    540
gcaggcggta tcatcctgct gttccaggac gacaaagtta gcggtctgca actgctgaaa    600
gatgaacagt ggatcgacgt cccgccgatg cgccattcga ttgtggtgaa tctgggcgac    660
cagttagaag tcattaccaa tggcaaatac aagagcgtgc tgcaccgtgt tattgcgcag    720
accgacggta cgcgcatgag cctggctagc ttttacaatc cgggtagcga cgccgttatc    780
tatccggcga aaaccctggt cgagaaagaa gcagaggaga gcactcaagt ttacccgaaa    840 tttgttttg atgattacat gaaactgtac gcaggtctga gtttccaggc gaaggaacca    900
cgttttgagg ctatgaaggc tatggagagc gatccgattg cctccgcgta ggtacc         956
```

\<210\> SEQ ID NO 3
\<211\> LENGTH: 25
\<212\> TYPE: DNA
\<213\> ORGANISM: Artificial Sequence
\<220\> FEATURE:
\<223\> OTHER INFORMATION: Oligonucleotide primer

\<400\> SEQUENCE: 3

```
catatgagct cagcaaaact cgatc                                            25
```

\<210\> SEQ ID NO 4
\<211\> LENGTH: 28
\<212\> TYPE: DNA
\<213\> ORGANISM: Artificial Sequence
\<220\> FEATURE:
\<223\> OTHER INFORMATION: Oligonucleotide primer

\<400\> SEQUENCE: 4

```
ctcgagttaa ccggtgatct cgaacagg                                          28

<210> SEQ ID NO 5
<211> LENGTH: 24
<212> TYPE: DNA
<213> ORGANISM: Artificial Sequence
<220> FEATURE:
<223> OTHER INFORMATION: Oligonucleotide primer

<400> SEQUENCE: 5
ccatggccga tccttttgtg gtgc                                              24

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 6
gtcgactaaa atgccaattt ggtcttg                                           27
```